United States Patent [19]

Suzuki et al.

[11] Patent Number: 5,677,450
[45] Date of Patent: Oct. 14, 1997

[54] ORGANIC ACID SALT OF MELAMINE, AND THERMOSETTING OR PHOTOCURABLE, THERMOSETTING COATING COMPOSITION USING THE SAME

[75] Inventors: Nobuyuki Suzuki, Tsurugashima; Kazunobu Fukushima, Saitama-ken; Kyo Ichikawa, Niiza; Teruo Saito, Iwatsuki; Hitoshi Inagaki, Saitama-ken, all of Japan

[73] Assignee: Taiyo Ink Manufacturing Co., Ltd., Tokyo, Japan

[21] Appl. No.: 743,969

[22] Filed: Nov. 5, 1996

Related U.S. Application Data

[62] Division of Ser. No. 394,812, Feb. 27, 1995, Pat. No. 5,604,080.

[30] Foreign Application Priority Data

Jan. 13, 1995 [JP] Japan .................. 7-19903

[51] Int. Cl.$^6$ .................................. C07D 251/00
[52] U.S. Cl. .................. 544/194; 544/195; 544/199; 544/200; 544/214; 544/215
[58] Field of Search .................. 544/194, 195, 544/199, 200, 214, 215; 430/280.1

[56] References Cited

U.S. PATENT DOCUMENTS

| | | | |
|---|---|---|---|
| 4,943,516 | 7/1990 | Kamayachi et al. | 430/280 |
| 5,093,223 | 3/1992 | Iwasawa et al. | 430/280 |
| 5,100,767 | 3/1992 | Yanagawa et al. | 430/280 |

FOREIGN PATENT DOCUMENTS 4-239070  8/1992  Japan .

*Primary Examiner*—Mark Chapman

*Attorney, Agent, or Firm*—Finnegan, Henderson, Farabow, Garrett & Dunner, L.L.P.

[57] ABSTRACT

Disclosed are an organic acid salt of melamine represented by the following general formula (1) and a thermosetting and a photocurable and thermosetting coating compositions containing the salt mentioned above.

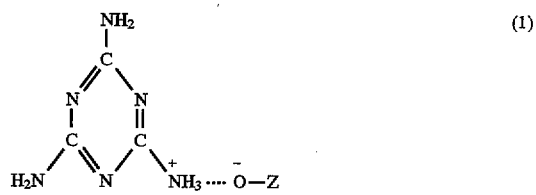

wherein Z represents

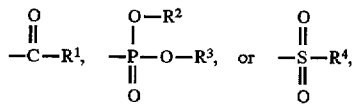

wherein $R^1$ represents a hydrogen atom or an alkyl group, alkylene group, alicyclic hydrocarbon, or aromatic hydrocarbon severally having from 1 to 18 carbon atoms, or any of said groups or hydrocarbons whose hydrogen atom is substituted by carboxyl group, hydroxyl group, or a halogen atom, $R^2$ represents a hydrogen atom or an alkyl group or alkylene group severally having from 1 to 9 carbon atoms, or any of said groups whose hydrogen atom is substituted by acryloyl group or methacryloyl group, $R^3$ represents an alkyl group or alkylene group severally having from 1 to 9 carbon atoms, or any of said groups whose hydrogen atom is substituted by acryloyl group or methacryloyl group, and $R^4$ represents an alkyl group or aromatic hydrocarbon severally having from 1 to 18 carbon atoms, or any of said group or hydrocarbon whose hydrogen atom is substituted by acryloyl group or methacryloyl group.

8 Claims, No Drawings

ORGANIC ACID SALT OF MELAMINE, AND THERMOSETTING OR PHOTOCURABLE, THERMOSETTING COATING COMPOSITION USING THE SAME

This is a division of application Ser. No. 08/394,812, filed Feb. 27, 1995, now U.S. Pat. No. 5,604,080.

BACKGROUND OF THE INVENTION

1. Field of the Invention

This invention relates to a novel organic acid salt of melamine and a thermosetting or a photocurable and thermosetting coating composition using the organic acid salt of melamine, and more particularly to a thermosetting or a photocurable and thermosetting coating composition serving advantageously as a solder resist which particularly excels in resistance to the action of electroless gold plating.

2. Description of the Prior Art

Owing to the recent rapid advance of semiconductor parts, the electronic devices have been showing the trend toward attaining reductions in size and weight, embodying improvements of performance, and undergoing diversifications of function and, as a consequence, the printed circuit boards have been tending toward increased density of printed circuits and adoption of the technique of mounting component elements on the surface of board (surface mount technology). For the purpose of coping with this densification of printed circuits and, in this connection, improving the reliability of the wiring laid between a pad disposed inside a printed circuit board and the component elements mounted on the surface of the printed circuit board, increasing specifications have been setting out the requirement that the pad be subjected to the electroless gold plating treatment. The thermosetting or the photocurable and thermosetting liquid solder resist commonly used, however, incurs the problem that, while the solder resist is being thermally cured, the resist is caused by the oxidation of a copper foil in the printed circuit board to lose the fast adhesiveness thereof to the copper foil and the part of the resist which borders on the site of the electroless gold plating inevitably peels off. Further, the thermal curing treatment entails the problem of so-called copper discoloration, namely the phenomenon that the copper foil is tarnished and impaired in appearance by the oxidation which occurs in the process of thermal curing.

U.S. Pat. No. 5,100,767 issued to Yanagawa et al. on Mar. 31, 1992 discloses a photosensitive resin composition which contains a carboxyl group-containing epoxy acrylate, tris(2, 3-epoxypropyl) isocyanurate, and a compound having a melamine skeleton. In this composition, the carboxyl group of the photosensitive resin gradually reacts with the compound having the melamine skeleton. When they are contained as mixed in the composition, the composition encounters problems with degradation of the stability with time and the developing property. When these components are supplied to the end user as two separate liquids and they are mixed by the end user in preparing the composition for use, this composition encounters problems with stability of viscosity of the produced mixture. Further, the basicity of the compound having the melamine skeleton accelerates the reaction of the carboxyl group of the photosensitive resin with the epoxy resin. When this composition is used as a photocurable and thermosetting liquid solder resist, therefore, it entails the problem that the freedom with which the management of drying is attained in the process of predrying of the resist (the condition of drying for allowing the development) is abridged.

SUMMARY OF THE INVENTION

An object of the present invention, therefore, is to provide a novel organic acid salt of melamine which has a rustproofing property and, particularly when incorporated in a liquid solder resist, can manifest such excellent effects as improving the adhesiveness of the resist to a copper foil laminated on a printed circuit board and the resistance thereof to the action of electroless gold plating and enhancing the storage stability (shelf life and pot life).

Another object of the present invention is to provide a thermosetting or a photocurable and thermosetting coating composition which excels in such various properties as resistance to the action of electroless gold plating, adhesiveness, resistance to the heat of soldering, resistance to chemicals, electric insulating property, and resistance to electrolytic corrosion which the solder resist prevalent in recent years is required to satisfy and, accordingly, proves useful as a solder resist sparingly incurring the phenomenon of copper discoloration in the process of thermal curing.

A more specific object of the present invention is to provide a thermosetting coating composition which is useful not only as a solder resist excelling in such properties as enumerated above but also as a marking ink and which is cleanable with an aqueous alkali solution.

Another more specific object of the present invention is to provide a photocurable and thermosetting coating composition which excels in a photocuring property besides such properties as enumerated above and proves useful as a photoimageable solder resist developable with an aqueous alkali solution, water, or a dilute aqueous acid solution.

To accomplish the objects mentioned above, the present invention provides an organic acid salt of melamine represented by the following general formula (1):

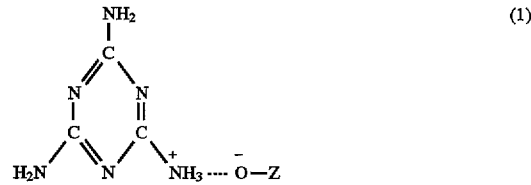

(1)

wherein Z represents

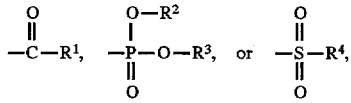

wherein $R^1$ represents a hydrogen atom or an alkyl group, alkylene group, alicyclic hydrocarbon, or aromatic hydrocarbon severally having from 1 to 18 carbon atoms, or any of the groups or hydrocarbons mentioned above whose hydrogen atom is substituted by carboxyl group, hydroxyl group, or a halogen atom, $R^2$ represents a hydrogen atom or an alkyl group or alkylene group severally having from 1 to 9 carbon atoms, or any of the groups mentioned above whose hydrogen atom is substituted by acryloyl group or methacryloyl group, $R^3$ represents an alkyl group or alkylene group severally having from 1 to 9 carbon atoms, or any of the groups mentioned above whose hydrogen atom is substituted by acryloyl group or methacryloyl group, and $R^4$ represents an alkyl group or aromatic hydrocarbon severally having from 1 to 18 carbon atoms, or any of the group or hydrocarbon mentioned above whose hydrogen atom is substituted by acryloyl group or methacryloyl group.

According to the present invention, there is further provided a liquid solder resist which contains such an organic acid salt of melamine as mentioned above. One aspect of the present invention consists in providing a thermosetting coating composition which comprises (A) varnish having a carboxyl group-containing resin dissolved in an organic solvent, (B) an epoxy compound containing at least two epoxy groups in the molecular unit thereof, and (C) an organic acid salt of melamine represented by the general formula (1) mentioned above. Another aspect of the present invention consists in providing a photocurable and thermosetting coating composition which comprises (a) a photocurable resin containing at least two ethylenically unsaturated bonds and a carboxyl group or an aprotic ammonium-containing group in the molecular unit thereof, (b) a photopolymerization initiator, (c) a diluent, (d) an epoxy compound containing at least two epoxy groups in the molecular unit thereof, and (e) an organic acid salt of melamine represented by the general formula (1) mentioned above.

DETAILED DESCRIPTION OF THE INVENTION

One example of the aforementioned organic acid salt of melamine (hereinafter referred to briefly as "melamine salt") is a melamine salt represented by the following general formula (2) which is obtained by the reaction of melamine with a carboxyl group-containing compound.

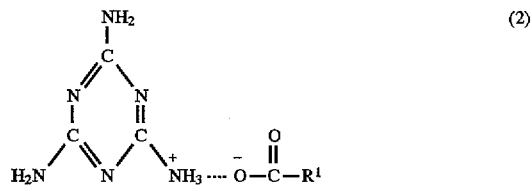

(2)

wherein $R_1$ represents a hydrogen atom or an alkyl group, alkylene group, alicyclic hydrocarbon, or aromatic hydrocarbon severally having from 1 to 18 carbon atoms, or any of the groups or hydrocarbons mentioned above whose hydrogen atom is substituted by carboxyl group, hydroxyl group, or a halogen atom.

Another example of the melamine salt mentioned above is a melamine salt represented by the following general formula (3) which is obtained by the reaction of melamine with an acid phosphoric ester.

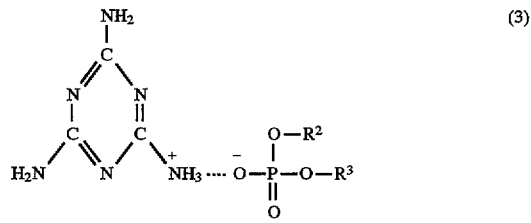

(3)

wherein $R^2$ represents a hydrogen atom or an alkyl group or alkylene group severally having from 1 to 9 carbon atoms, or any of the groups mentioned above whose hydrogen atom is substituted by acryloyl group or methacryloyl group, and $R^3$ represents an alkyl group or alkylene group severally having from 1 to 9 carbon atoms, or any of the groups mentioned above whose hydrogen atom is substituted by acryloyl group or methacryloyl group.

Yet another example of the melamine salt mentioned above is a melamine salt represented by the following general formula (4) which is obtained by the reaction of melamine with a sulfonic group-containing compound.

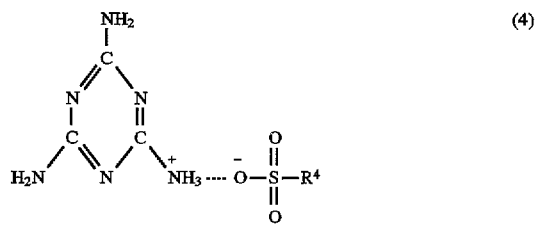

(4)

wherein $R^4$ represents an alkyl group or aromatic hydrocarbon severally having from 1 to 18 carbon atoms, or any of the group or hydrocarbon mentioned above whose hydrogen atom is substituted by acryloyl group or methacryloyl group.

These melamine salts are obtained by subjecting melamine to the neutralization reaction respectively with a carboxyl group-containing compound, an acid phosphoric ester, and a sulfonic group-containing compound in a solvent. These reactions proceed stoichiometrically in accordance with the following reaction formulas (5) through (7) and produce the corresponding melamine salts with the formation of an ionic bond between one of the amino groups of melamine and an organic acid.

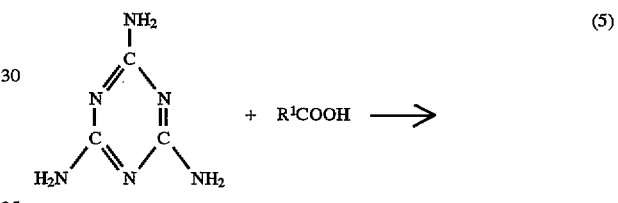

(5)

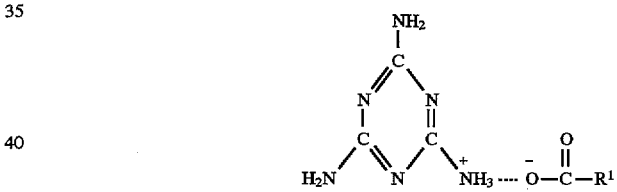

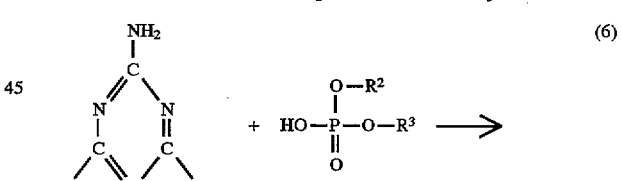

(6)

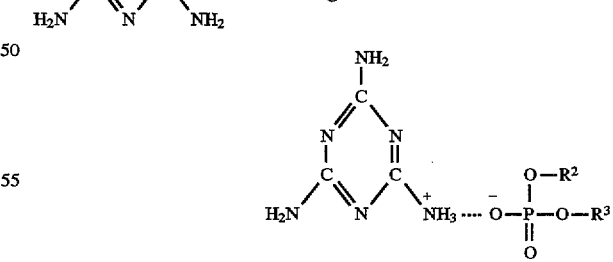

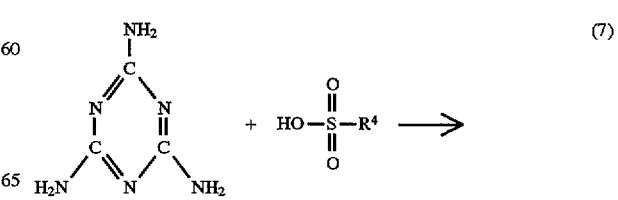

(7)

-continued

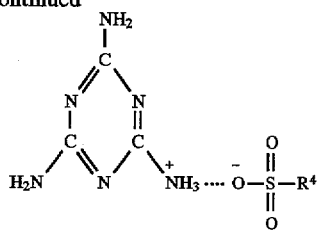

The solubility of melamine is about 0.32 g/100 ml of water at 20° C., about 1.34 g/100 ml of water at 50° C., and about 2.5 g/100 ml of water at the boiling point. The melamine, therefore, is used as dissolved in hot water of a temperature exceeding 50° C., desirably in hot water of a temperature exceeding 80° C., and most desirably in boiling water.

When the organic acid is directly added to the boiling water having melamine dissolved therein, the resultant mixture may possibly undergo the phenomenon of bumping due to the heat of neutralization. It is, therefore, desirable to have the organic acid diluted with a diluent in advance of the addition thereof to the boiling water. The diluents which are effectively usable for the purpose of this dilution include water, alcohols, and various hydrophilic solvents, for example. As the water, it is desirable to use deionized water for the sake of precluding the otherwise possible ingression of impurities.

Since one of the three amino groups in the molecular unit of melamine has high reactivity and the remaining two amino groups have low reactivity, the reaction of melamine with an organic acid proceeds stoichiometrically and, unless under severe reaction conditions such as high temperature and high pressure, produces a melamine salt having one molecule of the relevant organic acid added to one of the amino groups in the molecular unit of melamine. It suffices, therefore, to mix melamine with the organic acid at an equimolar ratio. The organic acid may be used in an excess of up to about 5%. The excess organic acid which remains in the unaltered form after the reaction can be removed by washing with water.

After completion of the reaction, the reaction mixture is cooled to induce precipitation of the melamine salt therein and the melamine salt is separated by filtration. Thus, the melamine salt aimed at by the present invention is obtained at a yield in the range of from 95 to 100%. By subjecting the produced melamine salt to thermal analysis (DSC), the difference in melting point of the product from the starting material and the question as to whether or not the product is a hydrate salt can be confirmed. Further, from the results of infrared spectroscopic analysis which indicate a clear shift of the absorption wavelength of the product from that of the starting material, the fact that the product is not a mixture can be confirmed. By the titration with KOH, a substance which has higher basicity than melamine and, therefore, brings about decomposition of melamine salt into melamine and a potassium salt of organic acid, the weight of the organic acid in the whole weight of the melamine salt can be determined and, as a result, the fact that the melamine salt is a salt having resulted from the combination of melamine with the organic acid at a molar ratio of 1:1 can be confirmed.

Examples of the carboxyl group-containing compounds mentioned above include, but are not limited to: monocarboxylic acids such as formic acid, acetic acid, propionic acid, butyric acid, lactic acid, glycolic acid, acrylic acid, and methacrylic acid; dicarboxylic acids such as oxalic acid, malonic acid, succinic acid, glutaric acid, adipic acid, sebacic acid, maleic acid, itaconic acid, phthalic acid, hexahydrophthalic acid, 3-methylhexahydrophthalic acid, 4-methylhexahydrophthalic acid, 3-ethylhexahydrophthalic acid, 4-ethylhexahydrophthalic acid, tetrahydrophthalic acid, 3-methyltetrahydrophthalic acid, 4-methyltetrahydrophthalic acid, 3-ethyltetrahydrophthalic acid, 4-ethyltetrahydrophthalic acid, and crotonic acid; and tricarboxylic acids such as trimellitic acid. The salt which is obtained by the equimolar reaction of melamine with a dicarboxylic acid among other carboxyl group-containing compounds proves particularly desirable in respect that the salt, when added to a solder resist, degrades the properties of the solder resist only sparingly. Then, in the case of a liquid solder resist using a carboxyl group-containing resin, it is desirable from the viewpoint of improving the storage stability of the liquid solder resist that the carboxylic acid used for the formation of the melamine salt be stronger than the carboxylic acid in the resin and, as a result, the salt be hardly allowed to yield to an exchange reaction. The carboxyl group-containing compound may be used, when necessary, in the form of a polybasic acid anhydride. Generally, polybasic acid anhydrides are easily allowed, when dissolved in boiling water, for example, to open their rings and form corresponding polycarboxylic acids.

Examples of the acid phosphoric esters mentioned above include, but are not limited to: monomethyl phosphate, dimethyl phosphate, monoethyl phosphate, diethyl phosphate, monopropyl phosphate, dipropyl phosphate, monobutyl phosphate, dibutyl phosphate, mono(2-acryloyloxyethyl) acid phosphate, di(2-acryloyloxyethyl) acid phosphate, mono(2-methacryloyloxyethyl) acid phosphate, and di(2-methacryloyloxyethyl) acid phosphate.

Examples of the sulfonic group-containing compounds mentioned above include, but are not limited to: methanesulfonic acid, p-toluenesulfonic acid, dodecylbenzenesulfonic acid, naphthalenesulfonic acid, and sulfoethyl methacrylate.

The melamine salt of the present invention possesses a rustproofing property and manifests the nature of decomposing itself into melamine and an organic acid at an elevated temperature in the approximate range of from 120° to 150° C. and can be advantageously used as an additive for improving the storage stability of a thermosetting or a photocurable and thermosetting coating composition particularly containing a carboxyl group-containing resin, enhancing the adhesiveness of the coating composition to a copper foil of a printed circuit board, and exalting the resistance of the composition to the action of electroless gold plating.

When melamine is added to a thermosetting or a photocurable and thermosetting coating composition containing a carboxyl group-containing resin, the melamine reacts with the carboxyl group of the resin to heighten the viscosity of the composition and impair the storage stability of the composition. Since melamine possesses basicity, it manifests the action of a curing catalyst in a composition of a curing system combining a carboxyl group-containing resin with an epoxy resin and an epoxy resin curing agent and consequently increases the viscosity of the composition. As a result, the printability of the composition is impaired and, at the same time, the freedom with which the drying of the composition is managed is abridged. On the contrary, since the present invention uses the melamine salt obtained by the reaction of melamine with an organic acid, it can diminish the basicity of melamine and consequently repress the reaction of melamine with the carboxyl group of the resin and, at the same time, prevent the melamine from functioning as a curing catalyst. The incorporation of the melamine salt of the present invention, therefore, prevents the composition from increasing the viscosity thereof, enables the composition to acquire improved printability, and augments the freedom with which the management of the drying is attained.

Further, in the photocurable and thermosetting coating composition, for example, the incorporation of melamine therein enables the composition to acquire improved adhesiveness to the printed circuit board. Though no fully convincing reason has been assigned for this improvement, the improvement may be logically explained as follows. When the composition is applied to a printed circuit board and heated to a temperature in the approximate range of from 80° to 100° C., for example, two of the three amino groups of the molecule of melamine form a chelate with the Cu atom of the copper foil in the printed circuit board and the remaining one amino group reacts with the carboxyl group of the photocurable resin or undergoes a Michael addition reaction with an acryloyl group thereof. The melamine, by thus coupling the copper foil with the resin as described above, is believed to enhance their mutual adhesiveness. If this reaction arises at the temperature of predrying, however, the problem of imperfect removal of the applied coating film of the composition from the unexposed area and inevitable persistence of part of the coating film thereon will be incurred after the coating film has been selectively exposed to the radiation of activated energy ray and then developed with a developing solution.

On the contrary, since the melamine salt of the present invention has a decomposition temperature in the approximate range of from 120° to 150° C. as described above, it is neither decomposed at the temperature of predrying nor suffered to induce the reaction or entail the problem mentioned above. When the applied coating film is thermally cured by being heated to a temperature in the approximate range of from 140° to 180° C., however, the melamine salt is decomposed into melamine and the organic acid and the liberated melamine, owing to the same reaction mechanism as mentioned above, serves the purpose of enhancing the adhesiveness of the cured coating film to the copper foil. Besides, since the melamine salt of the present invention has a rustproofing property, it is effective in curbing the oxidation of the copper foil in the printed circuit board in the process of thermal curing and preventing the phenomenon of so-called copper discoloration and also effective in further enhancing the adhesiveness of the cured coating film to the copper foil.

In addition thereto, since the melamine salt of the present invention is not decomposed to liberate melamine when the layer of coating applied to the printed circuit board is in the process of predrying, as described above, the freedom with which the drying is managed is augmented, i.e. the time and the temperature of the predrying can be set in wide ranges, which makes the operation easy.

The melamine salt according to the present invention can be made to manifest such outstanding functions and effects as mentioned above particularly when it is added to a thermosetting coating composition which contains (A) varnish having a carboxyl group-containing resin dissolved in an organic solvent and (B) an epoxy compound having at least two epoxy groups in the molecular unit thereof or a photocurable and thermosetting coating composition which contains (a) a photocurable resin having at least two ethylenically unsaturated bonds in the molecular unit and also having a carboxyl group or an aprotic ammonium-containing group, (b) a photopolymerization initiator, (c) a diluent, and (d) an epoxy compound having at least two epoxy groups in the molecular unit thereof.

The amount of the melamine salt to be added to the thermosetting or the photocurable and thermosetting coating composition is desired to be in the range of from 0.1 to 5.0% by weight, preferably in the range of from not less than 0.5% by weight to not more than 3% by weight, based on the total amount of the composition. If the amount of the melamine salt is less than 0.1% by weight, the copper foil of the printed circuit board will undergo heavy oxidation in the process of thermal curing and the adhesiveness of the cured coating film to the copper foil and the resistance of the cured coating film to the action of electroless gold plating will be acquired only with difficulty. Conversely, if the amount exceeds 5.0% by weight, the excess melamine salt will tend to persist in an unaltered form in the cured coating film and opacify the coating film.

Incidentally, as melamine salts which are similar to the organic acid salt of melamine according to the present invention, the phosphoric acid salt of melamine and the isocyanuric acid salt of melamine are now being manufactured on a commercial scale. To be used in a liquid solder resist, the phosphoric acid salt of melamine has problems with stability of viscosity, though it is effective in improving the resistance to the action of electroless gold plating. The isocyanuric acid salt of melamine owes the quality thereof as a salt to such strong bond as to adapt the salt for an organic filler and, therefore, avoids reacting with a carboxyl group-containing resin and lacks the ability to heighten the adhesiveness of the resist to the copper foil and improve the resistance to the action of electroless gold plating.

As the thermosetting coating composition to which the melamine salt of the present invention is to be added, various liquid solder resists which are well known and popularly used in the art may be adopted. For example, the thermosetting liquid solder resist composition which, as disclosed in published Japanese Patent Application, KOKAI (Early Publication) No. 4-239,070, comprises a main agent formed chiefly of varnish having a styrene-acrylic acid copolymer resin, namely a carboxyl group-containing resin, dissolved in an organic solvent and a hardener containing such powdery epoxy resin as triglycidyl isocyanurate and a small amount of a liquid epoxy resin may be cited. Since this thermosetting liquid solder resist contains a carboxyl group-containing resin, it can be washed with an aqueous alkali solution.

The styrene-acrylic acid copolymer resin mentioned above is desired to be (A-1) a copolymer comprising 10 to 50 mol % of acrylic acid or methacrylic acid, 30 to 80 mol % of a radically polymerizable monomer possessing a styrene skeleton, and 0 to 40 mol % of a radically polymerizable monomer copolymerizable therewith and having a weight-average molecular weight in the range of from 1,000 to 20,000 and an acid value in the range of from 100 to 300 mg KOH/g and/or (A-2) a copolymer comprising 20 to 50 mol % of maleic anhydride, 30 to 80 mol % of a radically polymerizable monomer possessing a styrene skeleton, and 0 to 40 mol % of a radically polymerizable monomer copolymerizable therewith, having half esterified with an aliphatic alcohol or an alcohol having an aromatic ring, and having a weight-average molecular weight in the range of from 1,000 to 20,000 and an acid value in the range of from 100 to 300 mg KOH/g.

The content of acrylic acid or methacrylic acid in the copolymer (A-1) mentioned above should be in the range of from 10 to 50 mol %. If the acrylic acid or methacrylic acid content is less than 10 mol %, the copolymer will not acquire fully satisfactory solubility in an aqueous alkali solution. Conversely, if this content exceeds 50 mol %, the produced cured coating film will exhibit inferior electrical properties. The range mentioned above, therefore, is just proper. For the similar reason, the content of maleic anhydride in the copolymer (A-2) should be in the range of from 20 to 50 mol %. As concrete examples of the radically polymerizable monomer possessing a styrene skeleton in the copolymer (A-1) and/or (A-2) mentioned above, styrene, a -methylstyrene, and vinyl toluene may be cited.

As concrete examples of the other copolymerizable and radically polymerizable monomer, methyl acrylate, methyl methacrylate, ethyl acrylate, ethyl methacrylate, benzyl acrylate, benzyl methacrylate, acrylonitrile, methacrylonitrile, methylvinyl ether, ethylvinyl ether, isobutylene, vinyl acetate, and vinyl pyrrolidone may be cited.

Either or both of the copolymers (A-1) and (A-2) mentioned above are dissolved in a suitable organic solvent to produce varnish. The concentration of the varnish is generally adjusted in the range of from 40 to 75% by weight. As concrete examples of the organic solvent to be used for the preparation of the varnish, diethylene glycol monobutyl ether, dipropylene glycol monomethyl ether, diethylene glycol monoethyl ether acetate, and propylene glycol monomethyl ether acetate may be cited. AS the epoxy compound (B) to be used as a thermosetting component mentioned above, any of the well-known epoxy resins (including epoxy oligomers) which has at least two epoxy groups in the molecular unit thereof may be used. As typical examples, the glycidyl ether type epoxy resins such as the bis-phenol A type epoxy resin obtained by the reaction of bis-phenol A with epichlorohydrin in the presence of an alkali, the epoxide of a resin resulting from the condensation of bis-phenol A with formalin, and the equivalent using bromated bis-phenol A in the place of bis-phenol A may be cited. Novolak type epoxy resins such as the phenol novolak type, orthocresol novolak type, and p-t-butyl phenol novolak type epoxy resins which are obtained by glycidyl-etherifying the corresponding novolak resins with epichlorohydrin may be also cited. Then, the bis-phenol F type and the bis-phenol S type epoxy resins obtained by the reaction of epichlorohydrin on bis-phenol F and bis-phenol S are other concrete examples. Further, alicyclic epoxy resins possessing a cyclohexene oxide group, a tricyclodecene oxide group, or a cyclopentene oxide group; glycidyl ester resins such as phthalic diglycidyl ester, tetrahydrophthalic diglycidyl ester, hexahydrophthalic diglycidyl ester, diglycidyl-p-oxybenzoic acid, and dimeric acid glycidyl ester; glycidyl amine type resins such as tetraglycidyl diamino-diphenyl methane, triglycidyl-p-aminophenol, diglycidyl aniline, diglycidyl toluidine, tetraglycidyl methaxylylene diamine, diglycidyl tribromoaniline, and tetraglycidyl bis-aminomethyl cyclohexane; hydantoin type epoxy resins having glycidyl groups linked to their hydantoin rings; and triglycidyl (or tris(2,3-epoxypropyl)) isocyanurates possessing a triazine ring are other examples. The epoxy resins mentioned above may be used either singly or in the form of a combination of two or more members. Among other epoxy resins mentioned above, it is desirable to use as a main component a finely powdered epoxy resin which exhibits sparing solubility in an organic solvent, such as bis-phenol S type epoxy resins represented by the product of Nippon Kayaku Co., Ltd. marketed under trademark designation of "EBPS"-200, that of Asahi Denka Kogyo K. K. under trademark designation of "EPX"-30, and that of Dai-Nippon Ink & Chemicals, Inc. under trademark designation of "EPICLON" EXA-1514; diglycidyl terephthalate resin represented by the product of Nippon Oil and Fats Co., Ltd. under trademark designation of "BLEMMER"-DGT; triglycidyl isocyanurate represented by the products of Nissan Chemical Industries, Ltd. under trademark designation of "TEPIC" and "TEPIC-H" and that of Ciba-Geigy Ltd. under trademark designation of "ARALDITE" PT810; and bixylenol type or biphenol type epoxy resins represented by the products of Yuka-Shell K. K. under trademark designation of "EPIKOTE" YX-4000 and YL-6121, in conjunction with a liquid epoxy resin.

The mixing ratio of the copolymer (A-1) and/or (A-2) mentioned above to the epoxy compound (B) can be suitably set. From the standpoint of the characteristic properties of the cured coating film, however, the mixing ratio is desired to be such that the proportion of the epoxy group falls in the range of from 1 to 1.5 mols per one mol of the carboxyl group of the copolymer.

The thermosetting coating composition of the present invention, when necessary, may incorporate therein any of well-known epoxy resin curing promotors for the purpose of promoting the curing reaction of the epoxy resin. Examples of the epoxy resin curing promotors include, but are not limited to: imidazole and imidazole derivatives such as 2-methylimidazole, 2-ethylimidazole, 2-ethyl-4-methylimidazole, 2-phenylimidazole, 4-phenylimidazole, 1-cyanoethyl-2-phenylimidazole, 1-(2-cyanoethyl)-2-ethyl-4-methylimidazole; guanamines such as acetoguanamine and benzoguanamine; and amines such as benzyldimethyl amine, 4-(dimethylamino)-N,N-dimethylbenzyl amine, 4-methoxy-N,N-dimethylbenzyl amine, and 4-methyl-N,N-dimethylbenzyl amine. The promotors which are commercially available include products of Shikoku Chemicals Co., Ltd. marketed under trademark designation of "CUREZOL" 2MZ-A, 2MZ-OK, 2PHZ, 2P4BHZ, and 2P4MHZ (invariably imidazole type compounds) and products of Sun-Apro K.K. marketed under product codes of U-CAT3503X, U-CAT3502X (invariably isocyanate compounds blocked with dimethyl amine), for example.

The thermosetting coating composition of the present invention which is prepared by adding the melamine salt of the present invention to the components mentioned above is easily dissolved in a dilute aqueous alkali solution having a pH value of not less than 11; such as an aqueous solution of 1% by weight of sodium carbonate or an aqueous solution of 1% by weight of potassium carbonate.

After this coating composition is printed in a prescribed pattern on a printed circuit board as by screen printing and thermally cured as by heating at a temperature in the range of from 130° to 180° C. thereby obtaining a cured coating film having the prescribed pattern, the screen printing plate and accessories thereof can be washed with an aqueous alkali solution. Since the washing of the screen printing plate and accessories has no use for an organic solvent, it does not pollute the environment, harm human bodies, or entail the danger of fire.

As the photocurable and thermosetting coating composition to which the melamine salt of the present invention is added, any of photocurable and thermosetting liquid solder resists well known and used popularly in the art may be similarly used. The composition which comprises (a-1) a photocurable resin having in combination at least two ethylenically unsaturated bonds and a carboxyl group in the molecular unit thereof or (a-2) a photocurable resin having in combination at least two ethylenically unsaturated bonds and a quaternary or aprotic ammonium-containing group in the molecular unit thereof obtained by the simultaneous reaction of an epoxy resin with a tertiary amine and a monocarboxylic acid possessing an ethylenically unsaturated bond, (b) a photopolymerization initiator, (c) a diluent, and (d) an epoxy resin is one example.

First, as the photocurable resin (a-1) mentioned above which has in combination at least two ethylenically unsaturated bonds and a carboxyl group in the molecular unit thereof, (1) the product obtained by the esterification of the epoxy group of a polyfunctional novolak type epoxy resin with the carboxyl group of an unsaturated monocarboxylic acid and the subsequent reaction of a saturated or unsaturated polybasic acid anhydride with the resultant hydroxyl group, (2) the product obtained by the reaction of (meth) acrylic acid with a copolymer composed of an alkyl (meth) acrylate and a glycidyl (meth)acrylate and the subsequent reaction of a saturated or unsaturated polybasic acid anhydride with the resultant reaction product, (3) the product obtained by the reaction of (meth)acrylic acid with a copolymer composed of a hydroxyalkyl (meth)acrylate, an alkyl (meth)acrylate, and a glycidyl (meth)acrylate and the subsequent reaction of a saturated or unsaturated polybasic acid anhydride with the resultant product, and (4) the product obtained by the partial reaction of a glycidyl (meth)acrylate with a copolymer composed of an alkyl (meth)acrylate and (meth)acrylic acid can be used, for example.

Since the photocurable resin (a-1) mentioned above has numerous free carboxyl groups added to the side chain of a backbone polymer, the composition containing this photocurable resin is developable with an aqueous alkali solution. When the applied coating film of the composition is developed after exposure to light and then postcured, the epoxy group of the epoxy resin (d) separately added to the composition as a thermosetting component copolymerizes with the free carboxyl groups in the side chain of the photocurable resin and converts the coating film into a solder resist film excellent in such properties as heat resistance, solvent resistance, acid resistance, adhesiveness, electric properties, and hardness.

The acid value of the photocurable resin (a-1) should be in the range of from 40 to 160 mg KOH/g. Preferably, this acid value is from 50 to 140 mg KOH/g in the resin (1), from 50 to 150 mg KOH/g in the resins (2) and (4), and from 40 to 120 mg KOH/g in the resin (3) mentioned above. Any deviation of the acid value from the aforementioned range is undesirable because the resin will manifest insufficient solubility in an aqueous alkali solution if the acid value is less than 40 mg KOH/g. Conversely, the acid value exceeding 160 mg KOH/g will give cause to deteriorate the various properties of the cured film such as resistance to alkalis and electrical properties expected of a resist.

The resin (1) mentioned above is obtained by causing the product of the reaction of such a novolak type epoxy resin as will be specifically described hereinafter with an unsaturated monocarboxylic acid to react with such a dibasic acid anhydride as phthalic anhydride or such an aromatic polycarboxylic anhydride as trimellitic anhydride or pyromellitic anhydride. In this case, the resin obtained by the reaction of at least 0.15 mol of a polybacic acid anhydride with each of the hydroxyl groups possessed by the reaction product of the novolak type epoxy resin with an unsaturated monocarboxylic acid proves to be suitable. When the number of ethylenically unsaturated bonds present in the molecular unit of the resin is small, the produced composition has a low speed of photocuring. It is therefore desired to use a novolak type epoxy resin as the raw material. A bis-phenol A type epoxy resin may be used in combination therewith for the purpose of lowering the viscosity of the ink.

Typical examples of the novolak type epoxy resins include phenol novolak type epoxy resins, cresol novolak type epoxy resins and novolak type epoxy resins of bisphenol A. The compounds which are obtained by causing epichlorohydrin to react with the corresponding novolak resins by the conventional method may be effectively used.

Examples of the unsaturated monocarboxylic acids mentioned above include, but are not limited to: acrylic acid, methacrylic acid, cinnamic acid, and the reaction product of a saturated or unsaturated dibasic acid anhydride with a (meth)acrylate having one hydroxyl group per molecule. These unsaturated monocarboxylic acids may be used either singly or in the form of a combination of two or more members. Among other monocarboxylic acids cited above, acrylic acid and methacrylic acid, particularly acrylic acid, prove to be particularly desirable from the viewpoint of the photocuring property.

Typical examples of the aforementioned acid anhydrides are dibasic acid anhydrides such as maleic anhydride, succinic anhydride, itaconic anhydride, phthalic anhydride, tetrahydrophtalic anhydride, hexahydrophthalic anhydride, methylhexahydrophthalic anhydride, endomethylenetetrahydrophthalic anhydride, methylendomethylenetetrahydrophthalic anhydride, chlorendic anhydride, and methyltetrahydrophthalic anhydride; aromatic polycarboxylic anhydrides such as trimellitic anhydride, pyromellitic anhydride, and benzophenone-tetracarboxylic dianhydride; and polycarboxylic anhydride derivatives such as 5-(2,5-dioxotetrahydrofuryl)-3-methyl-3-cyclohexene-1,2-dicarboxylic anhydride.

The copolymers which are base polymers of the resins (2) and (3) mentioned above are obtained by using as monomers such alkyl (meth)acrylates and glycidyl (meth)acrylates or further hydroxyalkyl (meth)acrylates and copolymerizing these monomers by any of the well-known methods such as, for example, the method of solution polymerization.

The alkyl (meth)acrylates mentioned above are alkyl esters of acrylic acid or methacrylic acid. The alkyl group of the alkyl esters is an aliphatic hydrocarbon radical having from 1 to 6 carbon atoms. Examples of alkyl (meth)acrylates include, but are not limited to: esters of acrylic acid or methacrylic acid with methyl, ethyl, propyl, isopropyl, butyl, and hexyl.

The hydroxyalkyl (meth)acrylates mentioned above are hydroxyalkyl esters of acrylic acid or methacrylic acid. The hydroxyalkyl group of these hydroxyalkyl esters is desired to be an aliphatic hydrocarbon radical having from 1 to 6 carbon atoms and containing a primary hydroxyl group. The reason for this desirability is that it is desirable to select and use a hydroxyalkyl (meth)acrylate containing a primary hydroxyl group as one of the component monomers of the aforementioned copolymer from the viewpoint of the ease with which the product of the reaction of the copolymer with (meth)acrylic acid is caused to react further with a polybasic acid anhydride. As typical examples of the hydroxyalkyl (meth)acrylates containing a primary hydroxyl group, 2-hydoxyethyl acrylate, 2-hydroxyethyl methacrylate, etc. may be cited. It should be noted, however, that these are not exclusive examples.

In the copolymer as the basis of the resin (2) mentioned above, the molar ratio of an alkyl (meth)acrylate to glycidyl (meth)acrylate is desired to be in the range of from 40:60 to 80:20. In the copolymer as the basis of the resin (3) mentioned above, the molar ratio of hydroxyalkyl (meth) acrylate to an alkyl (meth)acrylate to glycidyl (meth)acrylate is desired to be in the range of 10–50:10–70:20–60, preferably in the range of 15–30:30–50:30–50. If the proportion of glycidyl (meth)acrylate to the copolymer is unduly low from the lower limit of the range mentioned above, the copolymer will be at a disadvantage in acquiring an unduly low photocuring property. Conversely, if this proportion exceeds the upper limit of the range mentioned above, the copolymer will be at a disadvantage in failing to allow the reaction of synthesis of a photosensitive resin to proceed smoothly.

The degree of polymerization of the copolymer obtained by copolymerizing the component monomers, as expressed by weight-average molecular weight, is desired to be in the range of from 10,000 to 70,000, preferably from 20,000 to 60,000. If the weight-average molecular weight is less than 10,000, the composition containing the resin will be at a disadvantage in acquiring unduly low dryness to the touch of finger. Conversely, if it exceeds 70,000, the composition will be at a disadvantage in acquiring an unduly low developing property.

In the photocurable and thermosetting coating composition of the present invention, such vinyl compounds as styrene and methylstyrene may be used in a proportion not so large as to adversely affect the characteristic properties of the composition in addition to the component monomers mentioned above.

As the photocurable resin (a-2) possessing at least two ethylenically unsaturated bonds and a quaternary ammonium-containing group in the molecular unit thereof, the photocurable resin which, as disclosed in U.S. Pat. No. 5,093,223, has ethylenically unsaturated groups and an aprotic or quaternary ammonium-containing group incorporated in an aromatic epoxy resin may be cited.

The introduction of an ethylenically unsaturated group into the aromatic epoxy resin as described above can be performed by using a compound having both an ethylenically unsaturated bond and a functional group which can react on a functional group contained in the epoxy resin and by utilizing known techniques. For instance, (i) the addition reaction between carboxyl group and epoxy group, (ii) the addition reaction between hydroxyl group and epoxy group, and, when the epoxy resin contains hydroxyl group therein, (iii) the esterification reaction between hydroxyl group and carboxyl group, (iv) the addition reaction between isocyanate group and hydroxyl group, (v) the half esterification reaction between hydroxyl group and acid anhydride, or (vi) the ester exchange reaction between hydroxyl group and ester group can be utilized.

The reactions (i), (ii) and (iv), which are typical of the above-mentioned reactions, are described below in further detail.

Examples of the ethylenically unsaturated group- and carboxyl group-containing compounds which are usable in the above reaction (i) include, but are not limited to: (meth)acrylic acid, crotonic acid, itaconic acid monoalkyl esters, maleic acid monoalkyl esters and fumaric acid monoalkyl esters. Examples of the ethylenically unsaturated group- and hydroxyl group-containing compounds which are usable in the above reaction (ii) include 2-hydroxyethyl (meth)acrylate, 2-hydroxypropyl (meth)acrylate, allyl alcohol, N-methylol (meth)acrylamide and the other monohydric alcohols having an ethylenically unsaturated group.

Examples of the ethylenically unsaturated group- and isocyanate group-containing compounds which are usable in the above reaction (iv) are equimolar adducts between the ethylenically unsaturated group-containing monohydric alcohols mentioned above and a diisocyanate compound such as tolylene diisocyanate and isophorone diisocyanate. The addition of $\alpha,\alpha$-dimethyl-m-isopropenylbenzyl isocyanate to such monohydric alcohols may also be utilized.

The introduction of the quaternary ammonium-containing group into the aromatic epoxy resin as described above can be carried out, for example, by the method which comprises reacting a 1,2-epoxy group-containing resin simultaneously with a tertiary amine and an organic acid in the absence or presence of an inert organic solvent.

The above reaction among the epoxy resin, the tertiary amine and the organic acid is carried out under heating at about 40° to 80° C. and will be completed in about 1 to 20 hours.

The introduction of the quaternary ammonium-containing group into the aromatic epoxy resin can also be effected by the method which comprises reacting a 2-halogeno-1-hydroxyethyl group-containing resin with a tertiary amine in the absence or presence of an inert organic solvent, then converting the halogen atom to a hydroxyl group by anion exchange and reacting the resulting resin with an organic acid.

From the viewpoint of the photocuring property, the content of the aforementioned ethylenically unsaturated group in the photocurable resin should preferably be within the range of 0.1 to 10 mols, more preferably within the range of 0.2 to 5 mols, most preferably within the range of 1 to 4 mols, per kilogram of the resin (as solids). If the content of the ethylenically unsaturated group in the resin is less than 0.1 mol, the resin cannot be photocured to a satisfactory extent. Conversely, if this content exceeds 10 mols, mechanical properties of the cured product tend to decrease unfavorably.

The content of the above-mentioned aprotic ammonium-containing group should preferably be within the range of 0.1 to 5 mols, more preferably within the range of 0.1 to 2 mols, most preferably within the range of 0.2 to 1 mol, per kilogram of the resin (as solids). If the content of the aprotic ammonium-containing group in the resin is less than 0.1 mol, the curability of the resin tends to become insufficient. Conversely, when this content exceeds 5 mols, the water resistance of the cured product tends to become decreased unfavorably.

The detail of the aforementioned photocurable resin containing the aprotic ammonium-containing group or other onium-containing group is disclosed in U.S. Pat. No. 5,093,223 issued Mar. 3, 1992 to Iwasaki et al., the teachings of which are hereby incorporated by reference.

Typical examples of the photopolymerization initiators (b) mentioned above include benzoin and alkyl ethers thereof such as benzoin, benzoin methyl ether, benzoin ethyl ether, and benzoin isopropyl ether; acetophenones such as acetophenone, 2,2-dimethoxy-2-phenyl acetophenone, 2,2-diethoxy-2-phenyl acetophenone, 1,1-dichloroacetophenone, 1-hydroxycyclohexyl phenyl ketone, 2-methyl-1-[4-(methylthio)phenyl]-2-morpholinopropane-1-on, 2-benzyl -2-dimethylamino-1-(4-morpholinophenyl)-1-butanone; anthraquinones such as 2-methylanthraquinone, 2-ethylanthraquinone, 2-t-butyl anthraquinone, 1-chloroanthraquinone, and 2-amylanthraquinone; thioxanthones such as 2,4-dimethylthioxanthone, 2,4-diethylthioxanthone, 2-chlorothioxanthone, and 2,4-diisopropylthioxanthone; ketals such as acetophenone dimethyl ketal and benzyl dimethyl ketal; benzophenones such as benzophenone; and xanthones. These photopolymerization initiators may be used either singly or in the form of a combination of two or more members. Optionally such a photopolymerization initiator (b) may be used in combination with one or more well-known conventional photopolymerization accelerators such as of the benzoic acid type and the tertiary amine type.

The amount of the photopolymerization initiator (b) to be used suitably falls in the range of from 0.2 to 30 parts by weight, preferably from 2 to 20 parts by weight, based on 100 parts by weight of the photocurable resin (a-1 or a-2) mentioned above. If the amount of the photopolymerization initiator to be used is less than 0.2 part by weight, the composition will suffer from inferior photocuring property. Conversely, if the amount exceeds 30 parts by weight, the composition will entail the disadvantage of exhibiting inferior quality for cured film and poor stability during storage.

As the diluent (c) mentioned above, a photopolymerizable monomer and/or an organic solvent may be used.

Typical examples of photopolymerizable monomers include 2-hydroxyethyl acrylate, 2-hydroxypropyl acrylate, N-vinylpyrrolidone, acryloyl morpholine, methoxytetraethylene glycol acrylate, methoxypolyethylene glycol acrylate, polyethylene glycol diacrylate, N,N-dimethyl acrylamide, N-methylol acrylamide, N,N-dimethylaminopropyl acrylamide, N,N-dimethylaminoethyl acrylate, N,N-dimethylaminopropyl acrylate, melamine acrylate, diethylene glycol diacrylate, triethylene glycol diacrylate, propylene glycol diacrylate, dipropylene glycol diacrylate, tripropylene glycol diacrylate, polypropylene glycol diacrylate, phenoxyethyl acrylate, tetrahydrofurfuryl acrylate, cyclohexyl acrylate, trimethylol propane diacrylate, trimethylol propane triacrylate, glycerin diglycidyl ether diacrylate, glycerin triglycidyl ether triacrylate, pentaerythritol triacrylate, pentaerythritol tetraacrylate, dipentaerythritol pentaacrylate, dipentaerythritol hexaacrylate, isoborneolyl acrylate, cyclopentadiene mono- or di-acrylate, methacrylates corresponding to the acrylates enumerated abvoe, and mono-, di-, tri-, and higher polyesters of polybasic acids with hydroxyalkyl (meth)acrylates.

Examples of the organic solvents include, but are not limited to: ketones such as methylethyl ketone and cyclohexanone; aromatic hydrocarbons such as toluene, xylene, and Ipsol #150 (trademark for tetramethyl benzene-based petroleum solvent of Idemitsu Petrochemical Co., Ltd.); glycol ethers such as cellosolve, butyl cellosolve, carbitol, butyl carbitol, propylene glycol monomethyl ether, dipropylene glycol monomethyl ether; and acetates such as ethyl acetate, butyl acetate, cellosolve acetate, butyl cellosolve acetate, carbitol acetate, butyl carbitol acetate, propylene glycol monomethyl ether acetate, and dipropylene glycol monomethyl ether acetate.

The diluents (c) enumerated above can be used either singly or in the form of a mixture of two or more members. The amount of the diluent to be used is desired to fall in the range of 30 to 300 parts by weight, preferably 50 to 200 parts by weight, based on 100 parts by weight of the photocurable resin (a-1 or a-2) mentioned above.

Here, the aforementioned photopolymerizable monomer is used for the purpose of diluting the aforementioned photocurable resin thereby rendering the produced composition easily applicable, and imparting photopolymerizability upon the comosition. The amount of the monomer to be used is desired to fall in the range of 3 to 50 parts by weight, based on 100 parts by weight of the photocurable resin (a-1 or a-2) mentioned above. If the amount of the monomer is less than 3 parts by weight, the composition will be at a disadvantage in failing to enhance the photocuring property. Conversely, if the amount exceeds 50 parts by weight, the composition will be at a disadvantage in failing to heighten dryness to the tack-free touch of finger.

The organic solvent is used for the purpose of dissolving and diluting the photocurable resin (a-1 or a-2) mentioned above, allowing the resin to be applied in the from of a liquid, enabling the applied layer of the liquid to form a film by the predrying, and allowing the film to be exposed to light by the so-called "contact type exposure".

As concrete examples of the epoxy compound (d) to be used in the photocurable and thermosetting coating composition, the epoxy compounds enumerated as concrete examples of the epoxy compound (B) for use in the thermosetting coating composition may be cited. The composition, when necessary, may incorporate therein the epoxy resin curing promotor mentioned above.

The amount of the epoxy compounds (d) to be incorporated in the composition as a thermosetting component is desired to be in the range of 5 to 100 parts by weight, preferably 15 to 60 parts by weight, based on 100 parts by weight of the photocurable resin (a-1 or a-2) mentioned above.

The thermosetting or the photocurable and thermosetting coating composition of the present invention, when necessary for the purpose of acquiring improved resistance to the action of electroless gold plating, may further incorporate therein an amine type compound such as, for example, dicyan diamide, orthotollyl biguanide, guanidine compounds, and dimethyl urea.

For the purpose of enhancing the adhesiveness, the composition may incorporate therein a well-known inorganic filler such as, for example, barium sulfate, talc, silica, aluminum oxide, and aluminum hydroxide. The inorganic filler also imparts stable resistance to the action of electroless gold plating to the composition.

Further, the thermosetting or the photocurable and thermosetting coating composition of the present invention may incorporate therein, as an occasion demands, a well known and widely used color pigment such as phthalocyanine blue, phthalocyanine green, titanium oxide, and carbon black; a thickening agent such as organo-bentonite and finely powdered silica; an anti-foaming agent; a leveling agent; a coupling agent; a well known and widely used thermal polymerization inhibitor such as hydroquinone, hydroquinone monomethyl ether, pyrogallol, t-butyl catechol, and phenothiazine.

The photocurable and thermosetting coating composition which is prepared in accordance with the present invention is adjusted, when necessary, to a level of viscosity suitable for the coating method, applied by the technique of screen printing, curtain coating, spray coating, roll coating, or the like to a printed circuit board having a circuit already formed thereon, for example, and then predried at a temperature in the range of from 60° to 100° C., for example, thereby to evaporate the organic solvent from the coated composition and give rise to a tack-free coating film. Then, the composition coated on the printed circuit board is selectively exposed to an actinic ray through a photomask having a prescribed pattern and the composition in the unexposed areas of the coating film is developed with a dilute aqueous alkali solution to obtain a resist pattern. Thereafter, the photocured coating film is further thermally cured by subjecting to the heat treatment at a temperature in the range of from 140° to 180° C., for example. By this thermal treatment, in addition to the curing reaction of the aforementiond thermosetting components, the polymerization of the photocurable resin components is promoted and the copolymerization of this component with the thermosetting component are also facilitated so that the consequently produced resist film acquires improvements in various properties such as resistance to heat, resistance to solvents, resistance to acids, adhesiveness, electric properties, and hardness. The composition proves particularly useful for the formation of a solder resist. When the composition contains a photocurable resin having quaternary ammonium-containing group, it can be diluted with water and the unexposed areas of the coating film of the composition can be developed with water or a dilute aqueous acid solution of inorganic or organic acid.

As an aqueous alkali solution to be used in the process of development mentioned above, aqueous alkali solutions of potassium hydroxide, sodium hydroxide, sodium carbonate, potassium carbonate, sodium phosphate, sodium silicate, ammonia, amines, etc. can be used. As the dilute aqueous acid solution, inorganic acids such as hydrochloric acid and nitric acid; carboxylic acids such as acetic acid, formic acid, propionic acid, lactic acid, and glycolic acid; sulfonic acids such as p-toluene sulfonic acid; and acidic phosphoric esters can be used. Among other acid sources mentioned above, carboxylic acids prove to be particularly desirable in respect that even when they adhere to the surface of a photo-cured coating film, they are deprived of ionicity owing to their reaction with the epoxy group. From the standpoint of the smell, lactic acid and glycolic acid which are hydroxycarboxylic acids having high boiling points prove to be particularly desirable.

The concentration of the alkali or acid in the dilute aqueous alkali or acid solution is desired to be in the range of from 0.5 to 3% by weight in terms of the solubility of the composition in unexposed areas and the resistance of the photocured coating film to the attack by developing solution.

The light sources which are advantageously used for the purpose of photocuring the composition include low-pressure mercury lamp, medium-pressure mercury lamp, high-pressure mercury lamp, ultra-high-pressure mercury lamp, xenon lamp, and metal halide lamp, for example. The laser beam can be utilized as the actinic ray for exposure of the film.

As described above, the melamine salt of the present invention, when incorporated in a thermosetting or a photocurable and thermosetting coating composition, avoids reacting with the carboxyl group-containing resin and imparts highly satisfactory storage stability to the composition. When the resultant composition is thermally cured, the melamine salt is thermally decomposed because it has no such strong bond as is possessed by a melamine-isocyanuric acid salt and, consequently, a cured coating film manifesting as high adhesiveness to the copper foil and as high resistance to the action of electroless gold plating as is obtainable when melamine is added as a simple substance is produced.

The melamine salt of the present invention, when used in a solder resist containing a carboxyl group-containing resin and an epoxy resin, for example, exhibits lower basicity and lowered catalytic activity as compared with the incorporation of melamine as a simple substance and augments the freedom with which the control of drying is managed. Particularly in the liquid solder resist composed of a carboxyl group-containing photocurable resin and an epoxy resin, the melamine salt of the present invention imparts a wide freedom of management of drying and exalted workability to the solder resist.

The thermosetting or the photocurable and thermosetting coating composition useful as a solder resist which is obtained as described above can be adapted for such printed circuit boards as are specified to undergo an electroless gold plating which has been given in recent years to high density printed circuit boards having surface-mounted component parts.

Now, the present invention will be described more specifically below with reference to working examples of the invention and comparative examples. Wherever "parts" and "%" are mentioned hereinbelow, they invariably refer to those based on weight unless otherwise specified.

SYNTHESIS EXAMPLE 1

In a beaker having an inner volume of 2 liters, 800 ml of deionized water was charged and, with stirring pieces immersed therein, was stirred and boiled on a stirrer provided with a hot plate. In this hot water, 12.6 g of melamine was thoroughly dissolved. To the resultant hot solution, an aqueous solution prepared by diluting 9.0 g of lactic acid with 200 ml of deionized water was added and the resultant mixture was stirred. The resultant mixed solution, when concentrated with an evaporator and then cooled with ice water, precipitates crystals. The crystals were separated by filtration and then dried in a vacuum drier. By the thermal analysis (DSC) adapted to find changes in melting point and the infrared absorption analysis adapted to find changes in absorption wavelength, the crystals were confirmed to have formed a structure of salt. By the titration with KOH, the salt was confirmed to be composed of melamine and lactic acid at a molar ratio of 1:1. This salt will be referred to hereinafter as "melamine-lactic acid salt".

SYNTHESIS EXAMPLE 2

In a beaker having an inner volume of 2 liters, 800 ml of deionized water was charged and, with stirring pieces immersed therein, was stirred and boiled on a stirrer provided with a hot plate. In this hot water, 12.6 g of melamine was thoroughly dissolved. To the resultant hot solution, an aqueous solution prepared by diluting 10.4 g of malonic acid with 200 ml of deionized water was added and the resultant mixture was stirred. The resultant mixed solution, when concentrated with an evaporator and then cooled with ice water, precipitates crystals. The crystals were separated by filtration and then dried in a vacuum drier. By the thermal analysis (DSC), the infrared absorption analysis, and the titration with KOH performed in the same manner as in Synthesis Example 1, the crystals were confirmed to have formed a salt of melamine and malonic acid at a molar ratio of 1:1. This salt will be referred to hereinafter as "melamine-malonic acid salt".

SYNTHESIS EXAMPLE 3

In a beaker having an inner volume of 2 liters, 800 ml of deionized water was charged and, with stirring pieces immersed therein, was stirred and boiled on a stirrer provided with a hot plate. In this hot water, 12.6 g of melamine was thoroughly dissolved. To the resultant hot solution, an alcohol solution prepared by diluting 21.0 g of mono(2-methacryloyloxyethyl) acid phosphate with 200 ml of ethyl alcohol was added and the resultant mixture was stirred. The resultant mixed solution, when concentrated with an evaporator and then cooled with ice water, precipitates crystals. The crystals were separated by filtration and then dried in a vacuum drier. By the thermal analysis (DSC), the infrared absorption analysis, and the titration with KOH performed in the same manner as in Synthesis Example 1, the crystals were confirmed to have formed a salt of melamine and mono(2-methacryloyloxyethyl) acid phosphate at a molar ratio of 1:1. This salt will be referred to hereinafter as "melamine-PM salt".

SYNTHESIS EXAMPLE 4

In a beaker having an inner volume of 2 liters, 800 ml of deionized water was charged and, with stirring pieces immersed therein, was stirred and boiled on a stirrer provided with a hot plate. In this hot water, 12.6 g of melamine was thoroughly dissolved. To the resultant hot solution, an alcohol solution prepared by diluting 17.2 g of anhydrous p-toluenesulfonic acid with 200 ml of ethyl alcohol was added and the resultant mixture was stirred. The resultant mixed solution, when concentrated with an evaporator and then cooled with ice water, precipitates crystals. The crystals were separated by filtration and then dried in a vacuum drier. By the thermal analysis (DSC), the infrared absorption analysis, and the titration with KOH performed in the same manner as in Synthesis Example 1, the crystals were confirmed to have formed a salt of melamine and p-toluenesulfonic acid at a molar ratio of 1:1. This salt will be referred to hereinafter as "melamine-TSA salt".

SYNTHESIS EXAMPLE 5

In a beaker having an inner volume of 2 liters, 800 ml of deionized water was charged and, with stirring pieces immersed therein, was stirred and boiled on a stirrer provided with a hot plate. In this hot water, 12.6 g of melamine was thoroughly dissolved. Separately, in a beaker having an inner volume of one liter, 500 ml of deionized water was charged and, with stirring pieces immersed therein, was stirred and boiled on a stirrer provided with a hot plate. In this hot water, 15.2 g of tetrahydrophthalic anhydride was added and the resultant mixture was stirred for one hour with heating to give an aqueous solution of tetrahydrophthalic acid. This aqueous solution was added to the aqueous melamine solution mentioned above and the resultant mixture was stirred. The resultant mixed solution, when cooled with ice water, precipitates crystals. The crystals were separated by filtration and then dried in a vacuum drier. By the thermal analysis (DSC), the infrared absorption analysis and the titration with KOH performed in the same manner as in Synthesis Example 1, the crystals were confirmed to have formed a salt of melamine and tetrahydrophthalic acid at a molar ratio of 1:1. This salt will be referred to hereinafter as "melamine-THPA salt".

COMPARATIVE SYNTHESIS EXAMPLE 1

In a mortar, 12.6 g of melamine was pulverized and the resultant powder and 10.4 g of malonic acid added thereto were thoroughly pulverized and mixed. The mixture thus obtained will be referred to hereinafter as "melamine-malonic acid mixture".

EXAMPLE 1

In 40 g of carbitol acetate, 60 g of styrene-acrylic acid copolymer (produced by Johnson Polymer Corp. and marketed under trademark designation of "Johncryl-68") was heated until solution. The varnish thus obtained will be referred to hereinafter as "68 varnish".

The following components using the 68 varnish and the melamine-lactic acid salt obtained in Synthesis Example 1 were kneaded with a three-roll mill to obtain Composition A and Composition B. A thermosetting solder resist ink composition was obtained by mixing 200 parts of Composition A with 50 parts of Composition B.

| Composition A | |
| --- | --- |
| 68 varnish | 100 parts |
| Phthalocyanin green | 1 part |
| Silicone type anti-foaming agent (product of Shin-etsu Chemical Industry Co., Ltd. under product code of KS-66) | 1 part |
| Melamine-lactic acid salt | 3 parts |
| Barium sulfate | 70 parts |
| Finely powdered silica | 5 parts |
| Carbitol acetate | 20 parts |
| Total | 200 parts |
| Composition B | |
| Aqua Tohto 510 (trademark for water-soluble bisphenol A type epoxy resin of Tohto Kasei K.K.) | 15 parts |
| Triglycidyl isocyanurate | 20 parts |
| Talc | 8 parts |
| Carbitol acetate | 7 parts |
| Total | 50 parts |

EXAMPLE 2

The following components using the 68 varnish mentioned above and the melamine-TSA salt obtained in Synthesis Example 4 were kneaded with a three-roll mill to obtain Composition A and Composition B. A thermosetting solder resist ink composition was obtained by mixing 200 parts of Composition A with 50 parts of Composition B.

| Composition A | |
| --- | --- |
| 68 varnish | 100 parts |
| Phthalocyanin green | 1 part |
| Silicone type anti-foaming agent (KS-66) | 1 part |
| Melamine-TSA salt | 3 parts |
| Barium sulfate | 70 parts |
| Finely powdered silica | 5 parts |
| Carbitol acetate | 20 parts |
| Total | 200 parts |
| Composition B | |
| Aqua Tohto 510 | 15 parts |
| Triglycidyl isocyanurate | 20 parts |
| Talc | 8 parts |
| Carbitol acetate | 7 parts |
| Total | 50 parts |

EXAMPLE 3

In a four-necked flask equipped with a reflux condenser, a thermometer, and a stirrer, 215 g of cresol novolak type epoxy resin (produced by Dai-Nippon Ink & Chemicals, Inc. and marketed under trademark designation of "EPICRON N-680") and 204 g of carbitol acetate were heated until solution. The resin solution was heated to 85° C. and 1 g of tetrabutyl ammonium bromide and 0.1 g of hydroquinone were added thereto. The resultant mixture and 72 g of acrylic acid gradually added thereto dropwise were left reacting at 85° C. for 16 hours, to obtain epoxy acrylate. Then, the resultant reaction solution and 101 g of tetrahydrophthalic anhydride added thereto were left reacting at 85° C. for 6 hours. The varnish of the carboxyl group-containing epoxy acrylate thus obtained will be referred to hereinafter as "P varnish".

The following components using the P varnish and the melamine-malonic acid salt obtained in Synthesis Example 2 were kneaded with three-roll mill to obtain Composition A and Composition B. A photocurable and thermosetting solder resist ink composition was obtained by mixing 100 parts of Composition A with 25 parts of Composition B.

| Composition A | |
|---|---|
| P varnish | 60 parts |
| Pentaerythritol triacrylate | 5 parts |
| 2-Benzyl-2-dimethylamino-1-(4-morpholinophenyl)-1-butanone | 5 parts |
| Phthalocyanin green | 1 part |
| Melamine-malonic acid salt | 2 parts |
| Silicone type anti-foaming agent (KS-66) | 1 part |
| Barium sulfate | 20 parts |
| Finely powdered silica | 1 part |
| Carbitol | 5 parts |
| Total | 100 parts |

| Composition B | |
|---|---|
| Aqua Tohto 510 | 6 parts |
| Triglycidyl isocyanurate | 10 parts |
| Talc | 4 parts |
| Carbitol acetate | 5 parts |
| Total | 25 parts |

EXAMPLE 4

The following components using the P varnish obtained in Example 3 mentiond above and the melamine-THPA salt obtained in Synthesis Example 5 were kneaded with a three-roll mill to obtain Composition A and Composition B. A photocurable and thermosetting solder resist ink composition was obtained by mixing 100 parts of Composition A with 25 parts of Composition B.

| Composition A | |
|---|---|
| P varnish | 60 parts |
| Pentaerythritol triacrylate | 5 parts |
| 2-Benzyl-2-dimethylamino-1-(4-morpholinophenyl)-1-butanone | 5 parts |
| Phthalocyanin green | 1 part |
| Melamine-THPA salt | 3 parts |
| Silicone type anti-foaming agent (KS-66) | 1 part |
| Barium sulfate | 20 parts |
| Finely powdered silica | 1 part |
| Carbitol | 4 parts |
| Total | 100 parts |

| Composition B | |
|---|---|
| Aqua Tohto 510 | 6 parts |
| Triglycidyl isocyanurate | 10 parts |
| Talc | 4 parts |
| Carbitol acetate | 5 parts |
| Total | 25 parts |

EXAMPLE 5

In a four-necked flask equipped with a reflux condenser, a thermometer, and a stirrer, 215 g of cresol novolak type epoxy resin ("Epicron N-680") and 222 g of carbitol were heated until solution. The resin solution was heated to 60° C. and 46 g of N-ethyl morpholine and 0.1 g of hydroquinone were added thereto. The resultant mixture and 72 g of acrylic acid gradually added thereto dropwise were left reacting at 60° C. for 10 hours, to obtain water-soluble quaternary ammonium-containing epoxy acrylate. The varnish thus obtained will be referred to hereinafter as "W varnish".

The following components using the W varnish and the melamine-PM salt obtained in Synthesis Example 3 were kneaded with a three-roll mill to obtain Composition A and Composition B. A photocurable and thermosetting solder resist ink composition was obtained by mixing 100 parts of Composition A with 25 parts of Composition B.

| Composition A | |
|---|---|
| W varnish | 60 parts |
| 2-Benzyl-2-dimethylamino-1-(4-morpholinophenyl)-1-butanone | 5 parts |
| Phthalocyanin green | 1 part |
| Melamine-PM salt | 4 parts |
| Silica | 30 parts |
| Total | 100 parts |

| Composition B | |
|---|---|
| Dipentaerythritol hexaacrylate | 6 parts |
| TEPIC-H (trademark for high-melting type triglycidyl isocyanurate of Nissan Chemical Industries, Ltd.) | 10 parts |
| Finely powdered silica | 4 parts |
| Carbitol | 5 parts |
| Total | 25 parts |

COMPARATIVE EXAMPLE 1

The following components using the 68 varnish obtained in Example 1 were kneaded with a three-roll mill to obtain Composition A and Composition B. A thermosetting solder resist ink composition was obtained by mixing 200 parts of Composition A with 50 parts of Composition B.

| Composition A | |
|---|---|
| 68 varnish | 100 parts |
| Phthalocyanin green | 1 part |
| Silicone type anti-foaming agent (KS-66) | 1 part |
| Barium sulfate | 73 parts |
| Finely powdered silica | 5 parts |
| Carbitol acetate | 20 parts |
| Total | 200 parts |

| Composition B | |
|---|---|
| Aqua Tohto 510 | 15 parts |
| Triglycidyl isocyanurate | 20 parts |
| Talc | 8 parts |
| Carbitol acetate | 7 parts |
| Total | 50 parts |

COMPARATIVE EXAMPLE 2

The following components using the 68 varnish obtained in Example 1 were kneaded with a three-roll mill to obtain Composition A and Composition B. A thermosetting solder resist ink composition was obtained by mixing 200 parts of Composition A with 50 parts of Composition B.

| Composition A | |
|---|---|
| 68 varnish | 100 parts |
| Phthalocyanin green | 1 part |
| Silicone type anti-foaming agent-(KS-66) | 1 part |
| Melamine | 2 parts |
| Barium sulfate | 71 parts |
| Finely powdered silica | 5 parts |
| Carbitol acetate | 20 parts |
| Total | 200 parts |

-continued

| Composition B | |
|---|---|
| Aqua Tohto 510 | 15 parts |
| Triglycidyl isocyanurate | 20 parts |
| Talc | 8 parts |
| Carbitol acetate | 7 parts |
| Total | 50 parts |

COMPARATIVE EXAMPLE 3

The following components using the P varnish obtained in Example 3 and the melamine-malonic acid mixture obtained in Comparative Synthesis Example 1 were kneaded with a three-roll mill to obtain Composition A and Composition B. A photocurable and thermosetting solder resist ink composition was obtained by mixing 100 parts of Composition A and 25 parts of Composition B.

| Composition A | |
|---|---|
| P varnish | 60 parts |
| Pentaerythritol triacrylate | 5 parts |
| 2-Benzyl-2-dimethylamino-1-(4-morpholinophenyl)-1-butanone | 5 parts |
| Phthalocyanine green | 1 part |
| Melamine-malonic acid mixture | 2 parts |
| Silicone type anti-foaming agent (KS-66) | 1 part |
| Barium sulfate | 20 parts |
| Finely powdered silica | 1 part |
| Carbitol | 5 parts |
| Total | 100 parts |
| Composition B | |
| Aqua Tohto 510 | 6 parts |
| Triglycidyl isocyanurate | 10 parts |
| Talc | 4 parts |
| Carbitol acetate | 5 parts |
| Total | 25 parts |

Evaluation of Quality (1) Storage stability

Compositions A respectively of the examples and the comparative examples cited above were left standing at 25° C. for one month. At the end of the standing, they were examined as to change of viscosity with time. They were rated on the following four-point scale, wherein:

⊚: Within ±20% of ratio of change in viscosity
◯: From +20% to +40% of ratio of change in viscosity
Δ: From +40% to +100% of ratio of change in viscosity
×: More than +100% of ratio of change in viscosity The ink compositions obtained in Examples 1 and 2 and Comparative Examples 1 and 2 were each applied by the screen printing method onto a patterned copper-clad substrate in a prescribed pattern. Each coating film on the substrate was thermally cured at 150° C. for 40 minutes to prepare a test substrate.

The ink compositions obtained in Examples 3 and 4 and Comparative Example 3 were each applied by the screen printing method onto the entire surface of a copper-clad substrate having a prescribed pattern formed in advance thereon and then predried at 80° C. for 30 minutes to give a tack-free coating film. Each coating film on the substrate was exposed to an actinic ray according to a solder resist pattern through a negative film tightly superposed thereon and then developed with an aqueous 1 wt % sodium carbonate solution used as a developing solution and applied by spraying at a pressure of 1.5 kg/cm² to form a resist pattern thereon. The coating film on the substrate was thermally cured at 150° C. for 40 minutes to prepare a test substrate.

The ink composition obtained in Example 5 was applied by the screen printing method onto the entire surface of a copper-clad substrate having a prescribed pattern formed in advance thereon and then predried at 70° C. for 30 minutes to give a tack-free coating film. The coating film on the substrate was exposed to an actinic ray according to a solder resist pattern through a negative film tightly superposed thereon and then developed with a tap water used as a developing solution and applied by spraying at a pressure of 1.5 kg/cm² to form a resist pattern thereon. The coating film on the substrates was thermally cured at 150° C. for 40 minutes to prepare a test substrate.

The test substrates obtained as described above were tested for the following properties.

(2) Resistance to soldering temperature

A given test substrate was coated with a rosin type flux, immersed for 30 seconds in a soldering bath set in advance at 260° C., washed with propylene glycol monomethylether acetate for removal of the flux, and visually examined as to swelling, exfoliation, and discoloration of the resist layer. The rating was made on the following three-point scale, wherein:

◯: Perfect absence of discernible change
Δ: Only slight change
×: Swelled and exfoliated coating film (3) Resistance to the action of electroless gold plating The test substrates mentioned above were each subjected to electroless gold plating using commercially available electroless nickel plating solution and electroless gold plating solution.

The test substrates which had undergone the plating were subjected to a peel test using a cellophane adhesive tape as to the peel of resist. The rating was made on the following four-point scale, wherein:

⊚: Perfect absence of discernible change
◯: Very slight peel of coating film
Δ: Scattered spots of peel of coating film
×: Lines of peel of coating film The results of the tests indicated above are shown in the following table.

TABLE

| | Example | | | | | Comparative Example | | |
|---|---|---|---|---|---|---|---|---|
| Characteristic properties | 1 | 2 | 3 | 4 | 5 | 1 | 2 | 3 |
| (1) Storage stability | ◯ | ⊚ | ⊚ | ⊚ | ⊚ | ⊚ | × | × |
| (2) Resisrance to soldering temperature | ◯ | ◯ | ◯ | ◯ | ◯ | Δ | ◯ | ◯ |
| (3) Resistance to action of electroless gold plating | ⊚ | ◯ | ⊚ | ⊚ | ⊚ | × | ⊚ | Δ |

While certain specific working examples have been disclosed herein, the invention may be embodied in other specific forms without departing from the spirit or essential characteristics thereof. The described examples are therefore to be considered in all respects as illustrative and not restrictive, the scope of the invention being indicated by the appended claims rather than by foregoing description and all changes which come within the meaning and range of equivalency of the claims are, therefore, intended to be embraced therein.

What is claimed is:

1. An organic acid salt of melamine represented by the following general formula (1)

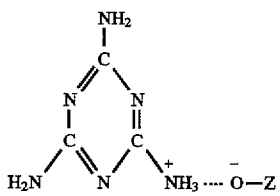
(1)

wherein Z represents

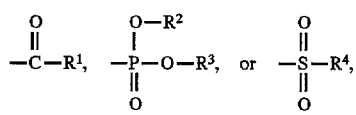

wherein $R^1$ represents a hydrogen atom or an alkyl group, alkylene group, alicyclic hydrocarbon, or aromatic hydrocarbon severally having from 1 to 18 carbon atoms, or any of said groups or hydrocarbons whose hydrogen atom is substituted by carboxyl group, hydroxyl group, or a halogen atom, $R^2$ represents a hydrogen atom or an alkyl group or alkylene group severally having from 1 to 9 carbon atoms, or any of said groups whose hydrogen atom is substituted by acryloyl group or methacryloyl group, $R^3$ represents an alkyl group or alkylene group severally having from 1 to 9 carbon atoms, or any of said groups whose hydrogen atom is substituted by acryloyl group or methacryloyl group, and $R^4$ represents an alkyl group or aromatic hydrocarbon severally having from 1 to 18 carbon atoms, or any of said group or hydrocarbon whose hydrogen atom is substituted by acryloyl group or methacryloyl group.

2. An organic acid salt of melamine obtained by the reaction of melamine with a carboxyl group-containing compound and represented by the following general formula (2)

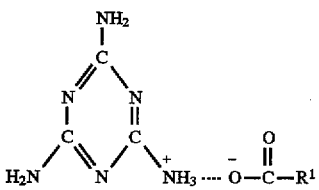
(2)

wherein $R_1$ represents a hydrogen atom or an alkyl group, alkylene group, alicyclic hydrocarbon, or aromatic hydrocarbon severally having from 1 to 18 carbon atoms, or any of said groups or hydrocarbons whose hydrogen atom is substituted by carboxyl group, hydroxyl group, or a halogen atom.

3. The organic acid salt of melamine according to claim 2, wherein said carboxyl group-containing compound is selected from the group consisting of formic acid, acetic acid, propionic acid, butyric acid, lactic acid, glycolic acid, acrylic acid, methacrylic acid, oxalic acid, malonic acid, succinic acid, glutaric acid, adipic acid, sebacic acid, maleic acid, itaconic acid, phthalic acid, hexahydrophthalic acid, 3-methylhexahydrophthalic acid, 4-methylhexahydrophthalic acid, 3-ethylhexahydrophthalic acid, 4-ethylhexahydrophthalic acid, tetrahydrophthalic acid, 3-methyltetrahydrophthalic acid, 4-methyltetrahydrophthalic acid, 3-ethyltetrahydrophthalic acid, 4-ethyltetrahydrophthalic acid, crotonic acid, trimellitic acid, and polybasic acid anhydrides of said polycarboxylic acids.

4. The organic acid salt of melamine according to claim 2, which is a salt obtained by the equimolar reaction of melamine with a dicarboxylic acid.

5. An organic acid salt of melamine obtained by the reaction of melamine with an acid phosphoric ester and represented by the following general formula (3)

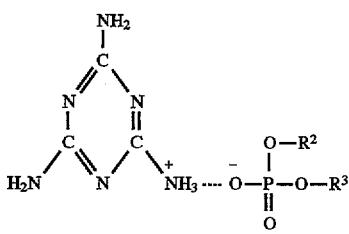
(3)

wherein $R^2$ represents a hydrogen atom or an alkyl group or alkylene group severally having from 1 to 9 carbon atoms, or any of said groups whose hydrogen atom is substituted by acryloyl group or methacryloyl group, and $R^3$ represents an alkyl group or alkylene group severally having from 1 to 9 carbon atoms, or any of said groups whose hydrogen atom is substituted by acryloyl group or methacryloyl group.

6. The organic acid salt of melamine according to claim 5, wherein said acid phosphoric ester is selected from the group consisting of monomethyl phosphate, dimethyl phosphate, monoethyl phosphate, diethyl phosphate, monopropyl phosphate, dipropyl phosphate, monobutyl phosphate, dibutyl phosphate, mono(2-acryloyloxyethyl) acid phosphate, di(2-acryloyloxyethyl) acid phosphate, mono(2-methacryloyloxyethyl) acid phosphate, and di(2-methacryloyloxyethyl) acid phosphate.

7. An organic acid salt of melamine obtained by the reaction of melamine with a sulfonic group-containing compound and represented by the following general formula (4)

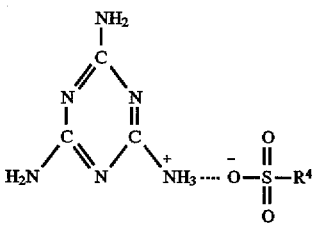
(4)

wherein $R^4$ represents an alkyl group or aromatic hydrocarbon severally having from 1 to 18 carbon atoms, or any of said group or hydrocarbon whose hydrogen atom is substituted by acryloyl group or methacryloyl group.

8. The organic acid salt of melamine according to claim 7, wherein said sulfonic group-containing compound is selected from the group consisting of methanesulfonic acid, p-toluenesulfonic acid, dodecylbenzenesulfonic acid, naphthalenesulfonic acid, and sulfoethylmethacrylate.

* * * * *